United States Patent [19]

Amini et al.

[11] Patent Number: 5,153,341

[45] Date of Patent: Oct. 6, 1992

[54] PROCESS FOR PREPARING BENZENESULFONATE SALTS

[75] Inventors: Bijan Amini, Moorestown, N.J.; Donald J. Dumas; George C. Sonnichsen, both of Wilmington, Del.

[73] Assignee: E. I. Du Pont de Nemours and Company, Wilmington, Del.

[21] Appl. No.: 674,400

[22] Filed: Mar. 25, 1991

[51] Int. Cl.$^5$ ............................................. C07C 303/32
[52] U.S. Cl. ........................................ 554/98; 554/97; 554/96; 558/268
[58] Field of Search ....................... 260/399, 400, 402; 558/268

[56] References Cited

U.S. PATENT DOCUMENTS

| | | | |
|---|---|---|---|
| 4,588,531 | 5/1986 | Balzer et al. | 260/402 |
| 4,588,533 | 5/1986 | Barry, Jr. | 260/402 |
| 4,788,316 | 11/1988 | Thornthwaite et al. | 260/402 |
| 4,985,180 | 1/1991 | Bellis et al. | 260/404 |

*Primary Examiner*—Jose G. Dees
*Assistant Examiner*—D. Deborah Carr
*Attorney, Agent, or Firm*—Charles E. Krukiel

[57] ABSTRACT

An improved process for preparing alkanoyloxyacetyloxybenzenesulfonate salts in which phenyl esters of alkanoyloxyacetic acids (alkanoyloxyacetyloxybenzenes) are sulfonated to yield novel alkanoyloxyacetyloxybenzenesulfonic acids which, on neutralization, yield the corresponding alkanoyloxyacetyloxybenzenesulfonate salts.

8 Claims, No Drawings

PROCESS FOR PREPARING BENZENESULFONATE SALTS

BACKGROUND OF THE INVENTION

The present invention relates to an improved process for preparing benzenesulfonate salts of the formula (I):

$$RCO_2CH_2CO_2PhSO_3M \qquad (I)$$

More particularly, the present invention relates to an improved process for preparing alkanoyloxyacetyloxybenzenesulfonate salts of formula (I), wherein $SO_3M$ is in the 4-position, from phenyl esters of acyloxyacetic acids (alkanoyloxyacetyloxybenzenes) of formula (II), by first sulfonating the phenyl ester and then neutralizing the intermediate sulfonic acid of formula (III):

$$RCO_2CH_2CO_2Ph \qquad (II)$$

$$RCO_2CH_2CO_2PhSO_3H \qquad (III)$$

Alkanoyloxyacetyloxybenzenesulfonate salts of formula (I) are known bleach activators and are described in greater detail in U.S. Pat. No. 4,778,618. The subject alkanoyloxyacetyloxybenzenesulfonate salts are conventionally prepared from the corresponding alkanoyloxyacetic acids by conversion to the corresponding acid chlorides followed by reaction with a salt of 4-hydroxybenzenesulfonic acid (i.e., 4-hydroxybenzenesulfonic acid, sodium salt) as taught in U.S. Pat. No. 4,778,618. Alternatively, salts of formula (I) may be prepared from salts of 4-(chloroacetyloxy)benzenesulfonic acid and alkanoic acids as described in U.S. Pat. No. 4,985,180. Thus, known processes for the preparation of compounds of formula (I) require the intermediacy of salts of 4-hydroxybenzenesulfonic acid. In practice, these processes can be complicated by the fact that alkali metal and alkaline earth metal salts of 4-hydroxybenzenesulfonic acid are relatively high melting solids with poor solubility in many commonly employed organic solvents.

The process of the present invention does not require a pre-formed salt of 4-hydroxybenzenesulfonic acid and is an all liquids process until the final step of neutralization which yields the solid product.

Phenyl esters of simple alkanoic acids are known to sulfonate on the aromatic ring as shown in Equation 1.

Equation 1:
$$RCO_2PH \xrightarrow{SO_3} RCO_2PhSO_3H$$

U.S. Pat. No. 4,588,533 describes a process for preparing acyloxybenzenesulfonic acids and the corresponding salts of formula (IV) wherein R is a hydrocarbyl radical containing up to about 30 carbon atoms and is selected from alkyl, alkenyl, cycloalkyl, aryl, aralkyl and alkaryl, and M is an alkali metal or an alkaline earth metal. In the first step of this process an acyloxybenzene is sulfonated with sulfur trioxide to give the acyloxybenzenesulfonic acid which is then neutralized with an alkali metal or an alkaline earth metal base to give the acyloxybenzenesulfonate salt of formula (IV).

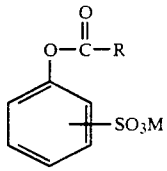
(IV)

German Patent Application 3,530,101 discloses a continuous process for the preparation of acyloxybenzenesulfonate salts of formula (V) wherein R is an aliphatic hydrocarbon which can contain from 1 to 17 carbon atoms, Y is hydrogen or an alkyl group containing from 1 to 18 carbon atoms and M is an alkali metal, an alkaline earth metal or substituted ammonium. In the first step of this process liquid acyloxybenzene is sulfonated with 0.9 to 1.3 molar equivalents of gaseous sulfur trioxide at 20°–200° C. and then held at 20°–70° C. for 5 to 180 minutes prior to being neutralized to give the acyloxybenzenesulfonate salts of formula (V).

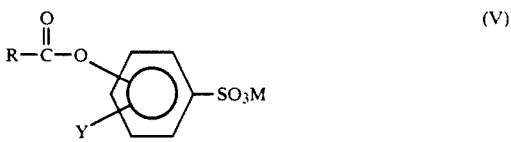
(V)

U.S. Pat. No. 4,692,279 discloses a process for preparing acyloxybenzenesulfonate salt by contacting acyloxybenzene with sulfur trioxide at a temperature ranging from about −20° to 50° C. to produce an intermediate reaction product which comprises about a 1:1 molar adduct of the sulfur trioxide and the acyloxybenzene, which is then digested at 25° to 75° C. for 0.1 to 4 hours prior to neutralization which then gives the acyloxybenzenesulfonate salt. The digestion step is described as being useful for controlling the exothermic rearrangement of the sulfur trioxide-acyloxybenzene adduct. Acyloxybenzenes are normally described as being of the formula (VI) where R is a saturated aliphatic group containing from about 2 to 19 carbon atoms inclusive.

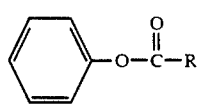
(VI)

U.S. Pat. No. 4,695,412 discloses a process for preparing acyloxybenzenesulfonic acids of formula (VII) and their alkali metal and alkaline earth metal salts wherein R is a straight-chain or branched saturated alkyl of from 5 to 11 carbon atoms. In the first step of this process a phenyl ester is sulfonated with sulfur trioxide or chlorosulfonic acid in a molar ratio of about 1:1 in the presence of 0.2 to 30 mole % (based on sulfur trioxide or chlorosulfonic acid) of a complexing agent for sulfur trioxide or chlorosulfonic acid.

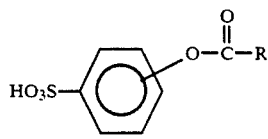
(VII)

U.S. Pat. No. 4,588,531 discloses a continuous process for neutralizing acyloxybenzenesulfonic acids of formula (VII) wherein R is a saturated or unsaturated alkyl radical of from 1 to 17 carbon atoms or is phenyl which is unsubstituted or monosubstituted or disubstituted by alkyl of from 1 to 3 carbon atoms, halogen, methoxy or nitro, to give the corresponding alkali metal and alkaline earth metal salts. In this process the liquid acyloxybenzenesulfonic acid and 5 to 50% strength by weight aqueous solution of an alkali metal or alkaline earth metal hydroxide, carbonate, or bicarbonate are simultaneously added into water at 0° to 60° C. with the pH of the water/reaction medium being maintained from 2.5 to 7.0. The salts are then isolated from the aqueous solutions using conventional techniques.

U.S. Pat. No. 4,788,316 discloses a process for preparing sulfonated esters and carbonates of formula (VIII) wherein R is a $C_1$-$C_{18}$ normal alkoxyl radical; $X_1$-$X_4$ may be hydrogens or one or more may be halogens, $C_1$-$C_4$ alkyl or alkoxyl radicals, RCOO— wherein R is defined as above, or $SO_3M$; and M is an alkali metal, alkaline earth metal or ammonium group. The process consists of (1) preparing the unsulfonated ester; (2) sulfonating the ester; and (3) neutralizing the resulting aromatic ester sulfonic acid. This disclosure teaches that high yields of acyloxybenzenesulfonates can be obtained if the neutralization is carried out in a non-aqueous organic solution with an alkali metal, alkali earth metal or ammonium carboxylate in an amount in excess over the amount needed to neutralize the sulfonic acid group(s) and any free or complexed $SO_3$ present in the product mixture from the sulfonation reaction.

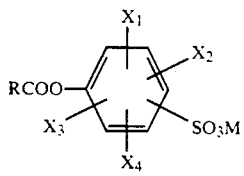
(VIII)

Treatment of alkyl esters of carboxylic acids with sulfonating agents followed by neutralization is known in the art to result in the formation of a variety of products, the nature of which is determined by the specific conditions which ar employed for the reaction. The sulfonation reactions of alkyl esters of carboxylic acids have been reviewed by B. L. Kapur et al. in *Journal of the American Oil Chemists' Society*, 1978, 55 (6), pp. 549-557, and by E. E. Gilbert in "*Sulfonation and Related Reactions*", Interscience Publishers, Wiley & Sons, Inc., NY, 1965, p. 36, the teachings of which are incorporated herein by reference. In general, these reactions result in the formation of products arising from alpha sulfonation and/or cleavage of the ester as illustrated generically in Equation 2 for sulfonation of a fatty acid methyl ester with sulfur trioxide followed by neutralization with sodium hydroxide. The mechanism of these reactions has recently been discussed by B. Fabry and B. Giesen in *Tenside Surf. Det.*, 1990, 27(4), pp. 243-248, the teachings of which are incorporated herein by reference.

Equation 2:

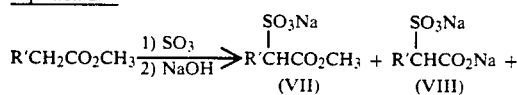

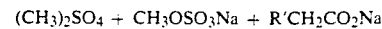

Due to the utility of alpha sulfonated esters as surfactants, there has been considerable interest in the development of processes which lead to the predominant formation of the alpha sulfonated esters of formula (VII); however, it has been proven to be difficult to avoid the formation of the dialkali metal salts of formula (VIII). By way of example, European Patent Application 153,016 describes a process for producing esters of formula (VII) which contain low levels of disalts of formula (VIII).

The sulfonation of phenyl esters of alkanoyloxyacetic acids of formula (II) does not appear to be known in the art. In addition, it is not clear from available references whether these diesters will undergo: (1) ring sulfonation reactions typical of phenyl esters, (2) alpha sulfonation and ester cleavage reactions typical of alkyl esters, or (3) some combination of these reactions. It has now been found that diesters of formula (II) can be sulfonated with selectivity for ring sulfonated products of formula (III). It has further been found that the products of formula (III) can be neutralized to give benzenesulfonate salts of formula (I).

SUMMARY OF THE INVENTION

The present invention is an improved process for preparing alkanoyloxyacetyloxybenzenesulfonate salts of the general formula (I):

wherein R is a linear or branched chain $C_5$-$C_{11}$ alkyl, and M is an alkali metal, an alkaline earth metal or ammonium radical. The process comprises sulfonating phenyl esters of alkanoyloxyacetic acids to form the intermediate alkanoyloxyacetyloxybenzenesulfonic acids, and then neutralization of the intermediate alkanoyloxyacetyloxybenzenesulfonic acids.

DETAILED DESCRIPTION OF THE INVENTION

According to the present invention, it is now possible to prepare alkanoyloxyacetyloxybenzenesulfonate salts of formula (I), wherein $SO_3M$ is preferentially in the 4-position, R is $C_5$-$C_{11}$ linear or branched alkyl and M is an alkali metal, an alkaline earth metal or an ammonium radical, by a substantially improved and more economical process than currently known:

The process of this invention is particularly useful in preparing bleach activators (I) wherein R is $C_7$-$C_9$ linear or branched alkyl.

According to the process of the present invention, the benzenesulfonate salts of formula (I) can be prepared in a two-step procedure as shown in Equation 3. This two-step procedure may be carried out as a stepwise batch process or as a continuous process.

Equation 3:
Step 1.

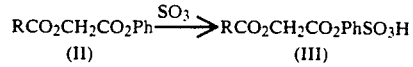

Step 2.

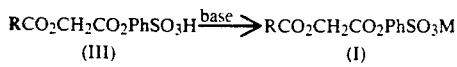
$$RCO_2CH_2CO_2PhSO_3H \xrightarrow{base} RCO_2CH_2CO_2PhSO_3M$$
(III) \qquad\qquad (I)

The phenyl esters of alkanoyloxyacetic acids (II) may be prepared by methods which are known in the art such as the reaction of alkanoyloxyacetic chlorides with phenol as described in U.S. Pat. No. 4,778,618. Alternatively, the phenyl ester (II) may be prepared by the treatment of phenyl chloroacetate with a $C_6$–$C_{12}$ carboxylic acid in the presence of a base as described in co-pending U.S. application Ser. No. 07/674,498, filed Mar. 25, 1991, and entitled "Improved Process for Preparing Phenyl Esters of Substituted Acids".

In the process of the present invention, the desired phenyl ester of an alkanoyloxyacetic acid of formula (II) is treated with a sulfonating agent by any method in which sulfur trioxide is made available to react with the phenyl ester to yield the ring sulfonated product of formula (III). Sulfonating agents which are known in the art and are suitable for use in practicing the invention include stabilized or unstabilized liquid sulfur trioxide, sulfur trioxide vapor, chlorosulfonic acid, sulfur trioxide complexes, oleum (sulfuric acid containing sulfur trioxide) and sulfamic acid. Preferred sulfonating agents include stabilized or unstabilized liquid sulfur trioxide, sulfur trioxide vapor, chlorosulfonic acid and sulfur trioxide complexes. More preferred sulfonating agents include stabilized or unstabilized liquid sulfur trioxide, sulfur trioxide vapor and sulfur trioxide complexes. Due to ease of processing on an industrial scale, the most preferred sulfonating agents are liquid sulfur trioxide, which can be stabilized or unstabilized, and sulfur trioxide vapor. When stabilized sulfur trioxide is employed, it is preferred that the stabilizing agent be removed prior to combining the sulfur trioxide with the diester of formula (II). The sulfonation may be carried out in the presence of a solvent which is relatively inert to sulfur trioxide or in the absence of a solvent. Low boiling solvents are preferred due to their ease of removal from the final product and because of their utility for removing heat generated during the course of the sulfonation reaction. Useful solvents for practicing the invention include sulfur dioxide, methylene chloride, ethylene dichloride, carbon tetrachloride, fluorotrichloromethane, dichlorotetrafluoroethane, trichloroethanes, trichlorotrifluoroethanes, dichlorotrifluoroethanes and heptane. Preferred solvents include sulfur dioxide, methylene chloride, ethylene dichloride and carbon tetrachloride. Sulfur dioxide is a particularly preferred solvent. In a preferred embodiment of the invention, the reaction is carried out in the absence of solvent.

The sulfonation may be carried out in a batch or continuous manner. Continuous film and continuous cascade reactors are particularly useful for carrying out the reaction when no solvent is to be used. When continuous film or continuous cascade reactors are employed, it is preferred that the sulfonating agent be gaseous sulfur trioxide. In such cases, it is also desirable to have the gaseous sulfur trioxide diluted with a relatively inert gas, such as, for example, nitrogen or dry air. Satisfactory results are achieved when the gas stream contains about 1–20% by volume sulfur trioxide, although 1–7% by volume sulfur trioxide is preferred.

Although any practical ratio of sulfur trioxide to the diester of formula (II) may be employed, it is preferred that between about 0.9 to 1.5 molar equivalents of sulfur trioxide be employed. In order to insure that a high level of sulfonation of the diester of formula (II) is achieved, it is more preferred that between about 1.0 and 1.3 molar equivalents of sulfur trioxide are employed. While it is generally most convenient to carry out the sulfonation at atmospheric pressure, the use of higher than atmospheric pressure may be beneficially employed to contain the solvent and/or the sulfonating agent.

The sulfonation reaction may be carried out at temperatures between about $-70°$ C. and $200°$ C. The optimum temperature for a given sulfonation will depend on a variety of factors including the exact nature of the diester of formula (II), the sulfonating agent employed and the solvent employed. The reaction is generally carried out at temperatures between $-30°$ C. and $100°$ C. with temperatures between $-20°$ C. and $50°$ C. being preferred for economy and convenience.

Upon completion of the addition of the sulfonating agent to the diester of formula (II) and prior to the neutralization step, it is usually necessary to hold the reaction mixture for a period of time sufficient to allow for the conversion of the diester of formula (II) to the sulfonic acid of formula (III) to proceed to an acceptable level of completion. The optimum hold time will depend on a variety of factors including the exact nature of the diester of formula (II) being sulfonated, the sulfonating agent employed, the temperature and the solvent employed; however, in general, hold times between 5 minutes and 4 hours will be required.

Sulfur trioxide complexing agents which may be employed in practicing the invention include, but are not limited to, those described in U.S. Pat. No. 4,695,412 and by E. E. Gilbert in "*Sulfonation and Related Reactions*", Interscience Publishers, Wiley & Sons, Inc., NY, 1965, pp. 7–18, the teachings of which are incorporated herein by reference. Typical examples of these complexing agents include dimethylformamide, diethylformamide, dibutylformamide, dimethylacetamide, dimethylbenzamide, 1-methyl-2-pyrrolidinone, 1-methyl-2-piperidone, ethyleneglycol dimethyl ether, dioxane, urea, tetramethylurea, pentamethylguanidine, imidazole, melamine, dimethylcyclohexylamine, succinimide, pthalimide, trimethylamine, triethylamine, dimethylaniline, diethylaniline, pyridine, polyvinylpyridine, 2-methylpyridine, 2,6-dimethylpyridine, N-ethylmorpholine, quinoline, thioxane, triethylphosphate and triphenylphosphine. When a sulfur trioxide complexing agent is employed in practicing the invention, the complex may be preformed or generated by the addition of either a catalytic or stoichiometric amount of complexing agent.

The intermediate sulfonic acids of formula (III) can be neutralized to give the corresponding alkanoyloxyacetyloxybenzenesulfonate salts of formula (I) by treating them with an alkali metal, alkaline earth metal, ammonium or amine base as shown in Equation 3. The neutralization may be carried out in either an aqueous system or in an anhydrous organic media; however, for reasons of cost and convenience, aqueous systems are preferred.

The bases which may be employed in the process of this invention include, but are not limited to, alkali metal carbonates, such as sodium carbonate and potassium carbonate; alkali metal bicarbonates, such as sodium bicarbonate; alkali metal hydroxides, such as sodium hydroxide and potassium hydroxide; alkali metal halides, such as sodium chloride and potassium chloride; alkali metal carboxylates, such as sodium acetate, alkali metal hydrides, such as sodium hydride, alkaline earth metal carbonates, alkaline earth metal hydroxides, such as magnesium hydroxide; alkaline earth metal halides; ammonium carbonates, such as ammonium carbonate; ammonium bicarbonates, such as ammonium bicarbonate; ammonium hydroxides, such as ammonium hydroxide and tetramethyl ammonium hydroxide; ammonium halides, such as ammonium chloride; ammonium carboxylates, such as ammonium acetate; amines; and relatively non-nucleophilic metal alkoxides, such as potassium tert-butoxide. Alkali metal carbonates and alkali metal hydroxides are preferred because of their lower costs with sodium carbonate, potassium carbonate, sodium hydroxide and potassium hydroxide being most preferred.

The term alkali metals as used herein refers to the Group 1a metals lithium, sodium, potassium, rubidium and cesium. The term alkaline earth metals refers to the Group 2a metals beryllium, magnesium, calcium, strontium and barium.

Due to the sensitivity of the sulfonic acid (III) to hydrolysis under alkaline or acidic conditions, it is advantageous to carry out the neutralization under conditions which minimize exposure of the product to high concentrations of aqueous base or acid and which also minimize exposure of the product to elevated temperatures. Neutralization at pH less than 9 and greater than 2.5 is preferred with a pH range of from 4 to 6 being most preferred. It is preferred that the neutralization be carried out at temperatures between −10° C. and 80° C. with temperatures between 0° C. and 50° C. being most preferred.

Control of the pH during the neutralization step may be most conveniently achieved by employing a buffer system. A particularly preferred buffer system involves the use of an aqueous sodium carbonate/sodium bicarbonate/carbonic acid system. This system may be prepared by dissolving the appropriate amount of carbonate and/or bicarbonate in water and adjusting the pH to the desired value by adding a suitable mineral acid. This method, however, requires solids material handling and necessitates dissolving of the buffer system components. An industrially convenient methods allows in situ generation of the buffer system by addition of sodium hydroxide to carbonic acid. The latter can be prepared by dissolving gaseous carbon dioxide in water. The pH of the buffer, prepared in manner described, can then be adjusted to the desired value by controlling the amount of caustic added to the carbonic acid. In the preferred embodiment of the present invention, the pH is adjusted to between 4 and 6. If desired, carbon dioxide can be sparged through the mixture while neutralization is in progress. It is found that by using the method described, one can easily maintain the pH within the desired range by controlling the feed rate of the base and sulfonic acid. A further advantage of this method is that, by monitoring and maintaining pH between 4 and 6, the measured pH is indicative that the added acid and the base are equimolar.

The neutralized product of formula (I) can be isolated by methods which are well known in the art such as filtration, evaporation, spray drying, freeze drying, drum drying or drying in a fluidized bed. In cases in which the sulfonation step of this process is incomplete, it may be possible to extract the unreacted material of formula (II) from the product of formula (III) using an organic solvent. Evaporation of the solvent would provide material of formula (II) which could be recycled to the first step of this process. In a preferred aspect, the extraction solvent and the step 1 solvent would be the same.

EXAMPLE

A 500 ml round-bottomed flask was charged with 29.2 g (0.01 mole) of nonanoyloxyacetic acid, phenyl ester, and 300 ml of methylene chloride and warmed at 30° to 35° C. while a stream of 8.8 g (0.11 mole) of $SO_3$ (generated in a separate vessel from 65% oleum) in nitrogen was bubbled through the methylene chloride solution over a period of 2 hrs. The resulting amber solution was then heated to reflux for 45 min. and then allowed to stand at ambient temperature for 17 hrs. The solution was then added dropwise to a solution of 9.0 g (0.11 mole) of sodium acetate in 75 ml of acetic acid containing 1 ml of acetic anhydride at 15° C. The precipitated solids were collected and dried in a vacuum oven at 60° C. to give 24.35 g of brown solid. HPLC analysis of this material indicated that it contained 35% by weight of nonanoyloxyacetyloxybenzenesulfonate, sodium salt. On standing, the filtrates yielded an additional 1.9 g of solid which analyzed as 25% by weight nonanoyloxyacetyloxybenzenesulfonate, sodium salt. Concentration of the filtrates provided an additional 10.1 g of material which analyzed as 13% by weight nonanoyloxyacetyloxybenzenesulfonate, sodium salt.

What is claimed:

1. An improved process for preparing alkanoyloxyacetyloxybenzenesulfonate salts of the general formula (I):

$$RCO_2CH_2CO_2PhSO_3M \qquad (I)$$

wherein R is a linear or branched chain $C_5$–$C_{11}$ alkyl, and M is an alkali metal, an alkaline earth metal or an ammonium radical which comprises (1) sulfonating a phenyl ester of the alkanoyloxyacetic acid with a sulfonating agent to form the corresponding intermediate alkanoyloxyacetyloxybenzenesulfonic acid and (2) neutralizing the intermediate.

2. The process of claim 1 wherein the sulfonating agent is selected from stabilized or unstabilized sulfur trioxide, sulfur trioxide vapor or sulfur trioxide complexes.

3. The process of claim 2 wherein the solvent is selected from sulfur dioxide, methylene chloride, ethylene dichloride or carbon tetrachloride.

4. The process of claim 2 wherein the solvent is sulfur dioxide.

5. The process of claim 1 wherein no solvent is employed and the sulfonating agent is sulfur trioxide vapor.

6. The process of claim 5 wherein the sulfur trioxide vapor is diluted with nitrogen or dry air to 1 to 20% by volume sulfur trioxide.

7. The process of claim 1 wherein the neutralization is carried out in an aqueous system using sodium carbonate, potassium carbonate, sodium hydroxide or potassium hydroxide as the base.

8. The process of claim 1 wherein the neutralization is carried out in a buffered system prepared from carbonic acid and sodium hydroxide and maintained at a pH of between 4 and 6.

* * * * *